(12) United States Patent
Iglesias et al.

(10) Patent No.: US 11,510,954 B2
(45) Date of Patent: Nov. 29, 2022

(54) METHOD FOR OBTAINING SAPONINS FROM PLANTS

(71) Applicant: Desert King Chile S.A., Quinta región (CL)

(72) Inventors: Leandro Padilla Iglesias, Quilpué (CL); Andres Valencia Michaud, Quilpué (CL)

(73) Assignee: DESERT KING CHILE S.A., Quinta Región (CL)

( * ) Notice: Subject to any disclaimer, the term of this patent is extended or adjusted under 35 U.S.C. 154(b) by 25 days.

(21) Appl. No.: 16/876,607

(22) Filed: May 18, 2020

(65) Prior Publication Data

US 2021/0060106 A1 Mar. 4, 2021

Related U.S. Application Data

(63) Continuation of application No. 15/777,891, filed as application No. PCT/US2016/060023 on Nov. 2, 2016, now Pat. No. 10,660,924.

(30) Foreign Application Priority Data

Nov. 25, 2015 (WO) ................ PCT/CL2015/000062

(51) Int. Cl.
*A61K 31/00* (2006.01)
*A61K 36/185* (2006.01)
(Continued)

(52) U.S. Cl.
CPC ............ *A61K 36/185* (2013.01); *A61K 36/25* (2013.01); *A61K 36/48* (2013.01); *A61K 36/73* (2013.01); *A61K 36/77* (2013.01); *A61K 36/896* (2013.01); *A61K 2236/00* (2013.01); *A61K 2236/15* (2013.01); *A61K 2236/17* (2013.01); *A61K 2236/331* (2013.01); *A61K 2236/53* (2013.01)

(58) Field of Classification Search
CPC ....................................................... A61K 31/00
See application file for complete search history.

(56) References Cited

U.S. PATENT DOCUMENTS 2,301,787 A 11/1942 Nord
2,960,500 A 11/1960 Holt et al.
(Continued)

FOREIGN PATENT DOCUMENTS

CL 200202573 11/2002
CL 50672 2/2015
(Continued)

OTHER PUBLICATIONS

Yin et al., "A comparative study of the effects of whole red ginseng extract and polysaccharide and saponin fractions on Influenza A (H1N1) virus infection," Biol Pharm Bull 36(6):1002-1006, 2013.*
(Continued)

*Primary Examiner* — Rosanne Kosson
(74) *Attorney, Agent, or Firm* — Knobbe, Martens, Olson & Bear, LLP

(57) ABSTRACT

The present application relates to a method for obtaining and purifying saponins from plant extracts, through a series of salting and filtrations steps, to provide high purity saponin extracts on large scale.

10 Claims, 3 Drawing Sheets

(51) Int. Cl.
*A61K 36/73* (2006.01)
*A61K 36/25* (2006.01)
*A61K 36/896* (2006.01)
*A61K 36/48* (2006.01)
*A61K 36/77* (2006.01)

(56) References Cited

U.S. PATENT DOCUMENTS

| | | | |
|---|---|---|---|
| 5,057,540 | A | 10/1991 | Kensil et al. |
| 6,355,249 | B2 | 3/2002 | Muir et al. |
| 7,884,195 | B2 | 2/2011 | Li |
| 10,660,924 | B2 | 5/2020 | Iglesias |
| 2002/0044940 | A1 | 4/2002 | Kensil |
| 2005/0233016 | A1 | 10/2005 | Hansen |
| 2014/0030318 | A1 | 1/2014 | Garcia et al. |

FOREIGN PATENT DOCUMENTS

| | | |
|---|---|---|
| CN | 1895313 | 1/2007 |
| CN | 101366721 | 2/2009 |
| CN | 101961427 A | 2/2011 |
| CN | 101747401 B | 3/2012 |
| CN | 102443072 A | 5/2012 |
| CN | 102697839 A | 10/2012 |
| WO | WO 00/37470 | 6/2000 |
| WO | WO 03/075939 | 6/2005 |
| WO | WO 14/086853 | 6/2014 |

OTHER PUBLICATIONS

English machine translation of Huang, Ken-Shung, JP 3930365 B2, 2007.*

Cheok et al., "Extraction and quantification of saponins: A Review," Food Research International (2014) vol. 59, pp. 16-40.

Xiang et al., "A study on the extraction and purification technology of tea sapogenin," African Journal of Biotechnology (2010) vol. 9, No. 18, pp. 2691-2696.

Extended European Search Report dated Oct. 10, 2018 for EP 16 869 047.7.

International Search Report and Written Opinion dated Jun. 10, 2016 for PCT/CL2015/000062—(Chile—Spanish).

International Preliminary Report on Patentability dated May 29, 2018 for PCT/US2016/60023.

International Search Report and Written Opinion dated Jan. 19, 2017 for PCT/US2016/60023.

* cited by examiner

METHOD FOR OBTAINING SAPONINS FROM PLANTS

BACKGROUND OF THE INVENTION

Field

The present application relates to the technical field of obtaining compounds from plants, in particular, providing methods for the production and purification of saponins from plants.

Description of Related Art

Saponins are compounds present in a wide variety of plants, having a chemical structure comprising a steroid or triterpenoid portion, attached to one or more sugar (saccharide) groups. The wide variety of chemical structures of saponins provides diverse physicochemical and biological characteristics, and therefore many industrial applications, such as in food, cosmetics, mining, agriculture, and pharmaceutical sectors.

To obtain products containing saponins, extraction and purification of these compounds from plant material is required. However, obtaining high-purity saponin extracts is technically difficult, both because of the diversity of saponin chemical structures, and because of the myriad of undesired compounds and impurities present in sources of saponins. For example, unwanted impurities, include, but not limited to phenolic compounds, proteins, carbohydrates and polysaccharides. The content of undesired impurities in the extract directly influences its industrial application. Indeed, the use of saponins in immunological applications requires a highly purified saponin, i.e., not containing any impurities that may adversely affect its pharmaceutical use.

There are various known methods for the purification of saponins, including solvent extraction, adsorption, ultrafiltration, or chromatography. For example, U.S. Patent Application Publication No. 2014/0030318 describes a method for purification of saponins using solubilizing compounds and exchange solvents, followed by dilution or dialysis. Chilean Patent Application No. CL 200202573 discloses a process for production of saponins by elimination of impurities with adsorbents, followed by filtration. Similarly, U.S. Pat. No. 6,355,249 describes purification of saponins by ultrafiltration, high performance liquid chromatography and reversed-phase chromatography.

However, the current purification methods are (i) not scalable to industrial levels; (ii) expensive; (iii) require excessively long periods for obtaining the purified saponins. For example, the production time of a batch of products based on 90% of saponins (based on dry solids) can take about 2 months using these conventional methods. Additionally, these processes are not capable of completely eliminating impurities, particularly the polysaccharides present in the plant extracts, because their large size prevents passage through ultrafiltration membranes. These polysaccharides may form undesirable precipitates during the storage of liquid saponin extracts, or when being used by the end user, and therefore are considered particularly negative attributes for purified saponins.

Consequently, new processes are required for obtaining highly purified saponins, which adequately eliminate polysaccharides, and other impurities, and that are efficient in both time and production costs.

SUMMARY OF THE INVENTION

Some embodiments provide a method for obtaining saponins from plants, comprising the steps of: providing a plant extract containing saponins and non-saponin polysaccharides, mixing the extract with a salt dissolved and/or suspended in solvent to form a mixture containing ion-polysaccharide complexes, adjusting the pH of the mixture, precipitating ion-polysaccharides complexes, filtering the precipitates, and clarifying the remaining solution to produce an extract of saponins. Consequently, the present application provides for elimination of impurities of plant extracts for quickly and reproducibly obtaining purified saponins, on an industrial scale, much faster than conventional methods.

Some embodiments provide a method for purifying saponins from plants, comprising providing a plant extract containing saponins; mixing the extract with a salt and a solvent to form a first solution, wherein the first solution comprises saponins and ion-polysaccharide complexes; adjusting the pH of the first solution to between 6 and 7; adding at least one phosphate to the first solution, thereby forming a first mixture that is substantially free of soluble ion-polysaccharides complexes; optionally heating the first mixture; filtering the first mixture to obtain a second solution; and clarifying the second solution to produce an extract of purified saponins.

In some embodiments, providing the plant extract containing saponins comprises providing a plant biomass; drying and grinding the biomass; and adding a solvent to the biomass.

In some embodiments, the biomass is obtained from plants selected from the families of Quillajaceae, Asparagaceae, Araliaceae, Fabaceae and Sapindaceae. In some embodiments, the biomass is obtained from species *Quillaja saponaria* Molina.

In some embodiments, the biomass is selected from plants at least 6 months old, at least 12 months old, at least 18 months old, at least 24 months old, at least 30 months old, at least 36 months old, at least 42 months old, at least 48 months old, at least 5 years old, at least 6 years old, at least 7 years old, at least 8 years old, at least 9 years old, at least 10 years old, at least 11 years old, at least 12 years old, at least 13 years old, at least 14 years old, at least 15 years old, at least 16 years old, at least 17 years old, at least 18 years old, at least 19 years old, at least 20 years old, at least 21 years old, at least 22 years old, at least 23 years old, at least 24 years old, at least 25 years old, at least 26 years old, at least 27 years old, at least 28 years old, at least 29 years old, at least 30 years old, at least 35 years old, at least 40 years old, at least 45 years old, at least 50 years old, at least 55 years old, at least 60 years old, at least 65 years old, at least 70 years old, at least 75 years old, at least 80 years old, or any combination thereof.

In some embodiments, the plant extract is provided as a solid. In some embodiments, the plant extract is provided as a solution. In some embodiments, the plant extract is provided as a slurry.

In some embodiments, the solvent is water. In some embodiments, the salt is calcium chloride. In some embodiments, adjusting the pH of the first solution comprises adding calcium hydroxide to the first solution. In some embodiments, the at least one phosphate is sodium hydrogen phosphate. In some embodiments, the method further comprises heating the first mixture to between 70° C. and 90° C.

In some embodiments, filtering the first mixture comprises a diatomaceous earth filter. In some embodiments, clarifying the second solution further comprises lowering the pH of the second solution to less than 7; adding at least one polymeric adsorbent and at least one clay-derived material; and removing the at least one polymeric adsorbent and at least one clay-derived material by filtration. In some embodiments, lowering the pH of the second solution comprises adding hydrochloric acid to the second solution.

In some embodiments, the at least one polymeric adsorbent is selected from bovine gelatin, fish gelatin, proteins from plant origin, albumin, milk proteins, polyvinylpyrrolidone (PVP), polyvinylpolypyrrolidone (PVPP), and combinations thereof. In some embodiments, the clay-derived material is bentonite. In some embodiments, removing the at least one polymeric adsorbent and at least one clay-derived material comprises a diatomaceous earth filter. Some embodiments further comprise further purification of the purified saponins, comprising one or more of nanofiltration, ultrafiltration and diafiltration, or combinations thereof.

Some embodiments provide an extract of purified saponins, which is obtained through the methods described herein.

DETAILED DESCRIPTION

Figure 1:
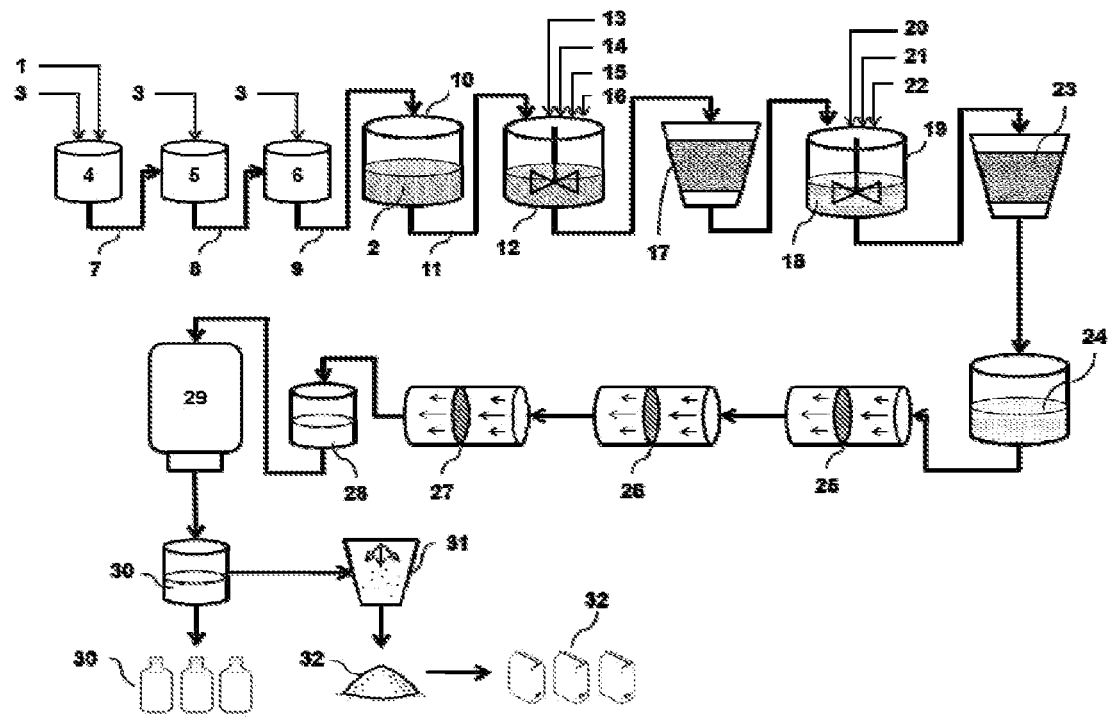
FIG. 1 is a schematic representation of the purification process of saponins from the bark of *Quillaja saponaria* Molina.

As described earlier, the present application relates to a process for obtaining and purification of saponins from plants, comprising extraction of saponins and subsequent elimination of impurities, particularly free polysaccharides (i.e., those polysaccharides not part of a saponin).

Surprisingly, the addition of a salt to a plant extract containing saponins, which forms ion-polysaccharide complexes with certain free polysaccharide impurities, but not with the sugar chains of saponins. This facilitates removal of ion-polysaccharide complexes, while saponins are maintained in solution.

In some embodiments, the precipitation is facilitated by adding one or more phosphates. In some embodiments, the precipitation is facilitated by adding a hydroxide base.

All technical terms used to describe the present application have the same meaning understood for a person with basic knowledge in the technical field in question. However, to define more clearly the scope of the application, a list of the terminology used in this description is included down below.

The term "saponin" must be understood as any glycoside characterized in that it comprises insoluble hydrophobic portion comprising a steroid or triterpenoid, and a hydrophilic portion comprising one or more saccharide chains. The saccharides can be any sugar, including, but not limited to glucose, arabinose, galactose, rhamnose, xylose, fucose, xylose, sucrose, lactose, maltose, trehalose, cellobiose, chitobiose, isomaltose, sophorose, sorbitol, mannitol, glucuronic acid and galacturonic acid.

The term "plant extract," as used herein, refers to any substance or derived product obtained by extraction from a part of a plant, through any method known in the art such as solvent extraction, adsorption, maceration, distillation, among others. A "plant extract" will also be considered as any product based on plant extracts that previously underwent a first extraction process and that can be found on sale to the general public, both as a liquid or a powder.

The term "biomass," as used herein, refers to any biological material originated from the kingdom Plantae. For example, the biomass can be the bark, trunk, leaves, stems, roots, seeds, flowers, fruits or a combination of any of them. In some embodiments, whole-plant biomass is used. "Whole-plant biomass" refers to at least that portion of the plant above the root (i.e., the trunk or stem, on up). In some embodiments, biomass comprises the bark, trunk, leaves, stems, roots, seeds, flowers, and/or fruits. In some embodiments, the biomass is bark. In some embodiments, the biomass is obtained from clonally grown whole plants. In some embodiments, the biomass is obtained from the bark, trunk, leaves, stems, roots, seeds, flowers, and/or fruits of clonally grown whole plants. In some embodiments, the biomass is bark from clonally grown whole plants.

The term "acid," as used herein, refers to a compound that can donate a proton or accept a pair of electrons. Examples of acids include, but are not limited to hydrochloric acid, hydrobromic acid, hydroiodic acid, hydrofluoric acid, perchloric acid, boric acid, sulfuric acid, phosphoric acid, nitric acid, a $C_1$-$C_6$ carboxylic acid, oxalic acid, lactic acid, malic acid, citric acid, benzoic acid, carbonic acid, methanesulfonic acid, and trifluoromethansulfonic acid.

The term "base," as used herein, refers to a compound that can accept a proton or donate a pair of electrons. Examples of bases include, but are not limited to ammonia, ammonium hydroxide, lithium hydroxide, sodium hydroxide, potassium hydroxide, barium hydroxide, magnesium hydroxide, calcium hydroxide, cesium hydroxide, lithium carbonate, sodium carbonate, potassium carbonate, barium carbonate, magnesium carbonate, calcium carbonate, cesium carbonate, lithium phosphate, sodium phosphate, potassium phosphate, barium phosphate, magnesium phosphate, calcium phosphate, cesium phosphate, pyridine, $C_1$-$C_6$ trialkyl amines, $C_1$-$C_6$ dialkyl amines, $C_1$-$C_6$ monoalkyl amines, imidazole, N-methylimidazole, benzimidazole, and histidine.

In some embodiments, the base is a hydroxide. In some embodiments, the base is sodium hydroxide. In some embodiments, the base is calcium hydroxide.

The term "impurity," as used herein, refers to any undesired substance in a solution or mixture, i.e., not the main chemical compound(s) or the compound(s) of interest. For the present application, the main compounds are saponins, and other substances present such as phenolic compounds (such as tannins, quercetin, leucocyanidin, kaempferol, among others), organic acids (such as caffeic acid, gallic acid, coumaric acid), free saccharides, free polysaccharides, lipids, and nitrogen-containing compounds, among others, are considered impurities.

The term "clarifying," as used herein, refers to the elimination of certain compounds which interact with other insoluble components by complexation, electric charges, entrainment or chemical reaction. Clarification can be accomplished by various techniques, including, but not limited to filtration through diatoms, by flocculation, or through the use of coagulants.

The term "free," as used herein, for example in "free polysaccharide" and "free phenolic compound," refers to compounds that are not part of a saponin. Thus, while saponins may contain one or more saccharide rings, such saccharides are not "free" saccharides.

As previously described, an object of the present application relates to methods and processes for obtaining saponins from plants, comprising: providing a plant extract containing saponins, adding a salt selected from the group of alkaline earth metals to the extract to form a first solution containing, among other compounds, ion-polysaccharide complexes, adjusting the pH of the first solution to between 6 and 7 and adding one or more phosphates to form a first mixture comprising saponins and ion-polysaccharides complexes, filtering the first mixture to obtain a second solution, and clarifying the second solution to produce an extract of purified saponins.

In some embodiments, biomass is selected based on its saponin profile. The desired saponin profile varies according to identity of the final product, for example, a food product, a vaccine, a plant growth stimulator, and an insecticide each have different desired saponin profiles. In some embodiments, the saponin profile is determined by HPLC, UPLC, or a combination thereof.

In some embodiments, obtaining the plant extract containing saponins comprises solvent extraction. Preferably, obtaining the plant extract used for the present application comprises: providing a biomass of a plant, drying and/or grinding the biomass, and adding a solvent to the biomass to obtain the extract. In some embodiments, the solvent is removed after obtaining the extract. In some embodiments, a continuous extractor is used.

In some embodiments, the plant biomass is dried prior to the extraction process. In some embodiments, the plant biomass is dried by the sun. In some embodiments, the plant biomass is heated to between about 20° C. to about 80° C. In some embodiments, the plant biomass is ground prior to the extract process. In some embodiments, the plant biomass is ground into pulp. In some embodiments, the plant biomass is ground into a slurry. In some embodiments, the plant biomass is ground to about 3.5 mesh. In some embodiments, the plant biomass is ground to about 4 mesh. In some embodiments, the plant biomass is ground to about 5 mesh. In some embodiments, the plant biomass is ground to about 6 mesh. In some embodiments, the plant biomass is ground to about 7 mesh. In some embodiments, the plant biomass is ground to about 8 mesh. In some embodiments, the plant biomass is ground to about 9 mesh. In some embodiments, the plant biomass is ground to about 10 mesh. In some embodiments, the plant biomass is ground to about 12 mesh.

In some embodiments, the solvent is a polar protic solvent. In some embodiments, the solvent is a polar aprotic solvent. In some embodiments the solvent is a non-polar solvent. In some embodiments, the solvent is selected from acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme, 1,2-dimethoxyethane, dimethylformamide, dimethylsulfoxide, 1,4-dioxane, ethanol, ethyl acetate, ethylene glycol, glycerin, heptane, hexamethylphosphoramide, hexamethylphosphorous triamde, hexane, methanol, methyl-t-butyl ether, methylene chloride, N-methyl-2-pyrrolidinone, pentane, perchloroethylene, petroleum ether, 1-propanol, 2-propanol, pyridine, tetrahydrofuran, toluene, triethylamine, trifluorotoluene, water, xylene, or any combination of the forgoing. In some embodiments the solvent is water.

In some embodiments, the biomass used in the present application is obtained from any plant containing saponins. Saponins are present in more than a hundred plant families, among which are mentioned the most relevant, such as: Quillajaceae, Asparagaceae, Dioscoreaceae, Liliaceae, Caryophyllaceae, Araliaceae, Leguminosae, Sapindaceae, Amaranthaceae, Aceraceae, Rhamnaceae, Hippocastanaceae, Cucurbitaceae, Araliaceae, Dennstaedtiaceae, among others. The amount of saponins contained in the plant and the type of existing chemical structure depends on the species, plant origin, and agronomic and environmental factors. For example, steroidal saponins are primarily found in monocots, while triterpenoid saponins are mainly found in dicotyledonous plants. The main plant saponins sources used for medical and industrial applications are alfalfa (*Medicago sativa*), horse-chestnut (*Aesculus hippocastanum*), liquorice (*Glycyrrhiza glabra*), yucca (*Yucca schidigera*), ginseng (*Panaxgenus*) and soap bark (*Quillaja saponaria*).

In some embodiments, the biomass is obtained from plants selected from the group of Quillajaceae, Asparagaceae, Araliaceae, Fabaceae and Sapindaceae. Preferably, the plant used corresponds to the species *Quillaja saponaria* Molina.

In some embodiments, the plant extract is obtained from about 1 kg of biomass to about 50,000 kg of biomass. In some embodiments, the plant extract is obtained from about 10 kg of biomass to about 40,000 kg of biomass. In some embodiments, the plant extract is obtained from about 100 kg of biomass to about 30,000 kg of biomass. In some embodiments, the plant extract is obtained from about 1,000 kg of biomass to about 20,000 kg of biomass. In some embodiments, the plant extract is obtained from about 1,500 kg of biomass to about 15,000 kg of biomass. In some embodiments, the plant extract is obtained from about 2,000 kg of biomass to about 10,000 kg of biomass. In some embodiments, the plant extract is obtained from about 2,500 kg of biomass to about 8,000 kg of biomass. In some embodiments, the plant extract is obtained from about 3,000 kg of biomass to about 6,000 kg of biomass. In some embodiments, the plant extract is obtained from about 4,000 kg of biomass to about 5,000 kg of biomass.

In some embodiments, the amount of solid plant extract is from about 1 kg to about 1,000 kg, from about 5 kg to about 950 kg, from about 10 kg to about 900 kg, from about 15 kg to about 850 kg, from about 20 kg to about 800 kg, from about 25 kg to about 750 kg, from about 30 kg to about 700 kg, from about 35 kg to about 650 kg, from about 40 kg to about 600 kg, from about 45 kg to about 550 kg, from about 50 kg to about 500 kg, from about 55 kg to about 450 kg, from about 60 kg to about 400 kg, from about 65 kg to about 350 kg, from about 70 kg to about 300 kg, from about 75 kg to about 350 kg, from about 80 kg to about 200 kg, from about 85 kg to about 150 kg, or from about 90 kg to about 100 kg.

In some embodiments, the amount of a solution or slurry plant extract is from about 500 L to about 50,000 L, from about 1,000 L to about 40,000 L, from about 2,000 L to about 30,000 L, from about 3,000 L to about 20,000 L, from about 4,000 L to about 10,000 L, from about 5,000 L to about 8,000 L, or from about 5,000 L to about 6,000 L.

In some embodiments, the salt is selected from an alkali metal salt, an alkaline earth salt, a transition metal salt, an ammonium salt, or combinations of the forgoing.

In some embodiments, the salt is selected from a lithium salt, a sodium salt, a potassium salt, a magnesium salt, a calcium salt, a strontium salt, a barium salt, a chromium salt, a manganese salt, an iron salt, a cobalt salt, a nickel salt, a copper salt, a zinc salt, an aluminum salt, a silver salt, or combinations of the foregoing. In some embodiments, the salt is selected from an alkali metal halide salt and an alkaline earth halide salt, or combinations thereof. In some embodiments, the salt is selected from $MgCl_2$, $CaCl_2$, $SrCl_2$, $BaCl_2$, $MgBr_2$, $CaBr_2$, $SrBr_2$, $BaBr_2$, or combinations thereof.

In some embodiments, the salt added to the plant extract to form the solution an alkaline earth metal salt. In some embodiments, the salt is calcium chloride ($CaCl_2$). In some embodiments, the salt is magnesium chloride ($MgCl_2$). In some embodiments, the salt is a water soluble inorganic calcium or magnesium salt. In some embodiments, the salt is a food grade calcium or magnesium salt.

In some embodiments, the pH of the mixture is adjusted to between about 2 and 10, to between about 3 and 9, to between about 4 and 8, to between about 5 and 7, to between about 6 and 7, to between about 6 and 8, to between about 6 and 9, to between about 6 and 10, to between about 2 and 7, to between about 3 and 7, to between about 4 and 7, to between about 3 and 4, or to between about 4 and 5.

In some embodiments, the one or more phosphates are alkali metal phosphates. In some embodiments, the one or more phosphates are alkaline earth phosphates. In some embodiments, the one or more phosphates are selected from lithium phosphate, sodium phosphate, potassium phosphate, barium phosphate, magnesium phosphate, calcium phosphate, cesium phosphate, lithium hydrogen phosphate, sodium hydrogen phosphate, potassium hydrogen phosphate, barium hydrogen phosphate, magnesium hydrogen phosphate, calcium hydrogen phosphate, cesium hydrogen phosphate, lithium dihydrogen phosphate, sodium dihydrogen phosphate, and potassium dihydrogen phosphate.

In some embodiments, the one or more phosphates added are preferably sodium hydrogen phosphate ($Na_2HPO_4$), but can be any of sodium phosphates, such as sodium dihydrogen phosphate ($NaH_2PO_4$), sodium phosphate ($Na_3PO_4$) or sodium hydrogen bisphosphate ($Na_2H_2PO_7$).

In some embodiments, the mixture from which a precipitate of ion-polysaccharides complexes is obtained, is subjected to a heat treatment consisting of heating the mixture. In some embodiments, the mixture is heated to at least about 30° C.; at least about 35° C.; at least about 40° C.; at least about 45° C.; at least about 50° C.; at least about 55° C.; at least about 60° C.; at least about 65° C.; at least about 70° C.; at least about 75° C.; at least about 80° C.; at least about 85° C.; at least about 90° C.; at least about 95° C.; at least about 100° C.; at least about 105° C.; or at least about 110° C. In some embodiments, the mixture is heated to between about 50° C. to about 100° C. In some embodiments, the mixture is heated to between about 60° C. to about 90° C. In some embodiments, the mixture is heated to between about 70° C. to about 90° C.

In some embodiments, the mixture is heated for about 30 minutes. In some embodiments, the mixture is heated for about 60 minutes. In some embodiments, the mixture is heated for about 90 minutes. In some embodiments, the mixture is heated for about 120 minutes. In some embodiments, the mixture is heated for about 150 minutes. In some embodiments, the mixture is heated for about 180 minutes. In some embodiments, the mixture is heated for about 210 minutes. In some embodiments, the mixture is heated for about 240 minutes. In some embodiments, the mixture is heated for about 270 minutes. In some embodiments, the mixture is heated for about 300 minutes.

In some embodiments, precipitating ion-polysaccharides complexes comprises calcium or magnesium complexes with one or more pectins, starches, xylans, proteins, or combinations thereof.

In some embodiments, the precipitate is filtered through silica, alumina, celite, diatomaceous earth, perlite, or combinations thereof. In some embodiments, the precipitate is filtered with a filter selected from candle filters, filters of recessive plates, plate and frame filters, cartridge filters, depth filters, decanters, disc filters, cellulose plate filters, industrial centrifuges, rotating drum filters, or combinations thereof.

In some embodiments, clarifying the remaining solution comprises one or more of the steps described herein, followed by filtration.

In some embodiments, clarifying the remaining solution comprises decreasing the pH of the solution to less than 7. In some embodiments, clarifying the remaining solution comprises decreasing the pH of the solution to less than 6. In some embodiments, clarifying the remaining solution comprises decreasing the pH of the solution to less than 5. In some embodiments, clarifying the remaining solution comprises decreasing the pH of the solution to less than 4. In some embodiments, clarifying the remaining solution comprises decreasing the pH of the solution to less than 3.

In some embodiments, clarifying the remaining solution comprises adding polymeric adsorbents to the remaining solution. In some embodiments, the polymeric adsorbents comprise gelatin, albumin, milk proteins, polyvinylpyrrolidone (PVP), polyvinylpolypyrrolidone (PVPP), or combinations thereof.

In some embodiments, clarifying the remaining solution comprises adding a clay-derived material to the remaining solution. In some embodiments, the clay-derived material comprises sodium bentonite, calcium bentonite or combinations thereof After this filtration process, an extract of purified saponins is obtained. Optionally, the extract can be concentrated by any filtration technique known in the prior art. Preferably, the concentration of the extract of purified saponins is carried out by nanofiltration, ultrafiltration and diafiltration, or any combination of these techniques.

With the purpose of giving saponins extracts a longer shelf life, a pasteurization process can be performed optionally to the extract of purified saponins, by means of any standard method of pasteurization known in the state of the art, such as pasteurization VAT, HTST, UHT, or combinations thereof.

After this process, a product comprising the extract of purified, concentrated and pasteurized saponins is obtained in a liquid form. Optionally, the liquid product can be transformed to a powder product, by any technique already known in the prior art. Preferably, the process through which a powder product is generated is by spray drying or pulverization.

The stages or steps of the present application must not be considered as sequential steps and therefore can be performed in an order different than described. For example, the plant extract can be clarified prior to the step of adding calcium salts, finally obtaining the same extract of purified saponins compared to the process performed in the aforementioned order.

In some embodiments, the saponin extract is at least about 50% pure. In some embodiments, the saponin extract is at least about 55% pure. In some embodiments, the saponin extract is at least about 60% pure. In some embodiments, the saponin extract is at least about 65% pure. In some embodiments, the saponin extract is at least about 70% pure. In some embodiments, the saponin extract is at least about 75% pure. In some embodiments, the saponin extract is at least about 80% pure. In some embodiments, the saponin extract is at least about 85% pure. In some embodiments, the saponin extract is at least about 90% pure. In some embodiments, the saponin extract is at least about 95% pure. In some embodiments, the saponin extract is at least about 98% pure. In some embodiments, the saponin extract is at least about 99% pure. In some embodiments, the saponin extract is at least about 99.5% pure. Some representative saponin structures are shown in Table 1.

TABLE 1

| Compound | Chemical Structure |
|---|---|
| QS-21 | 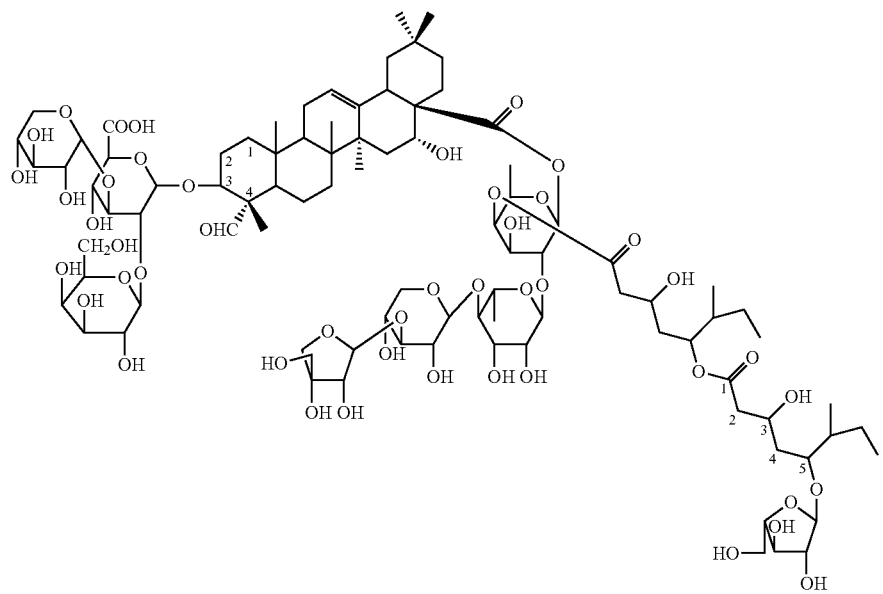 |
| QS-18 | 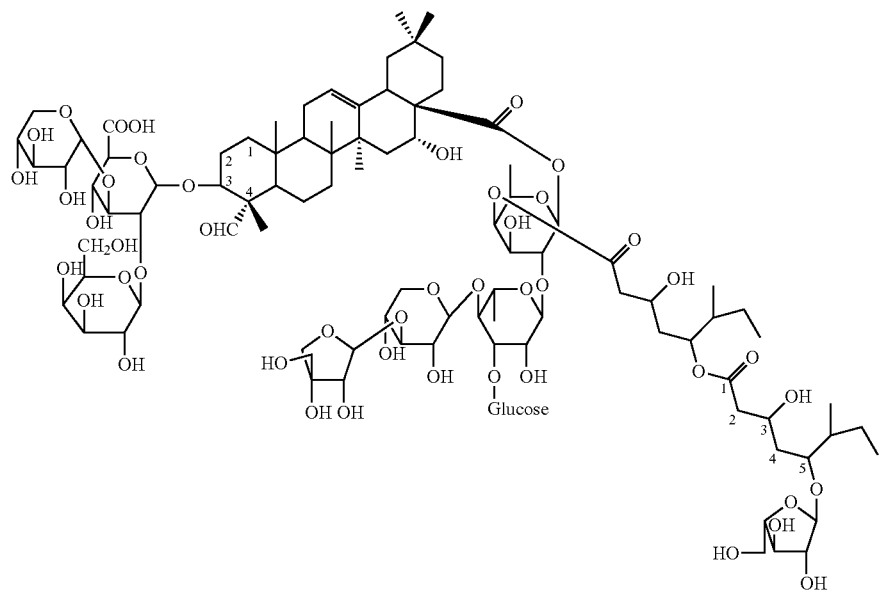 |

TABLE 1-continued
Compound Chemical Structure
DS-1
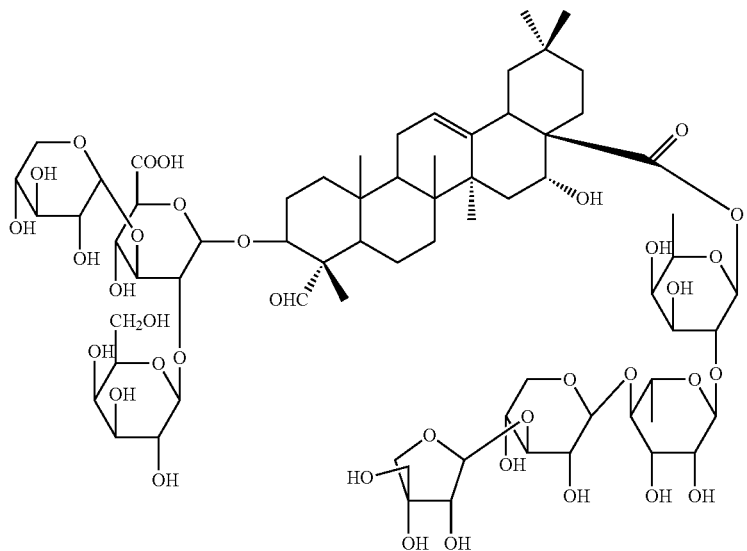
DS-1(R)
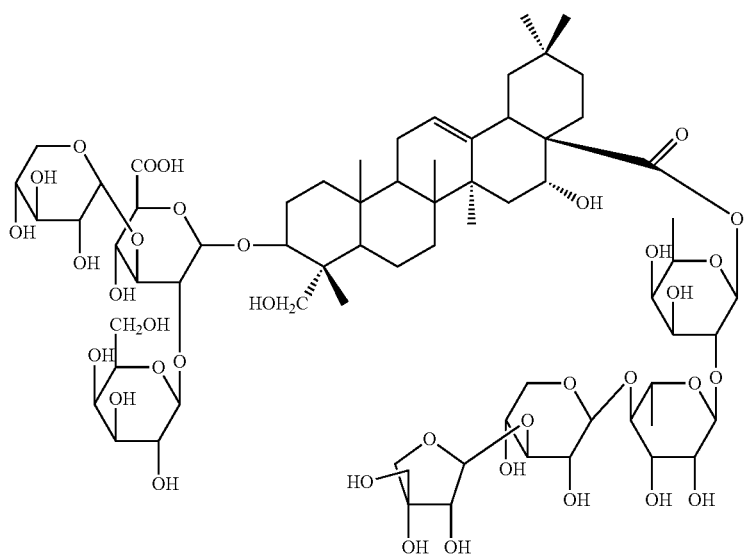

TABLE 1-continued

| Compound | Chemical Structure |
|---|---|
| DS-2 | 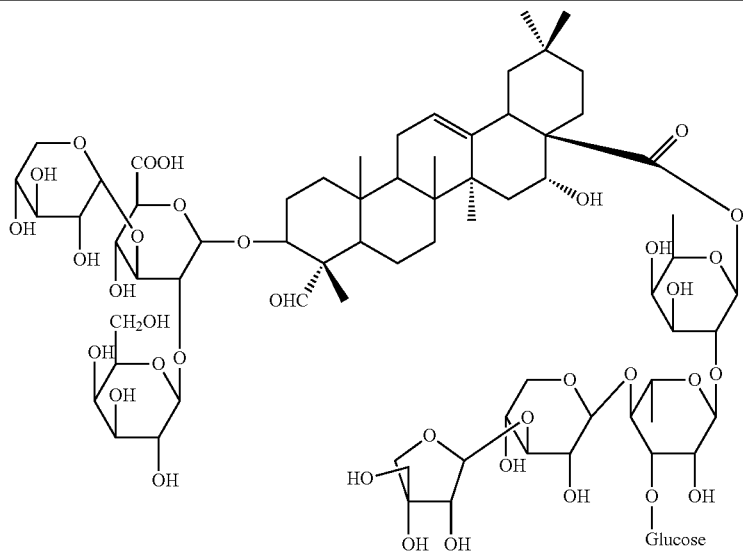 |
| QH-957 | 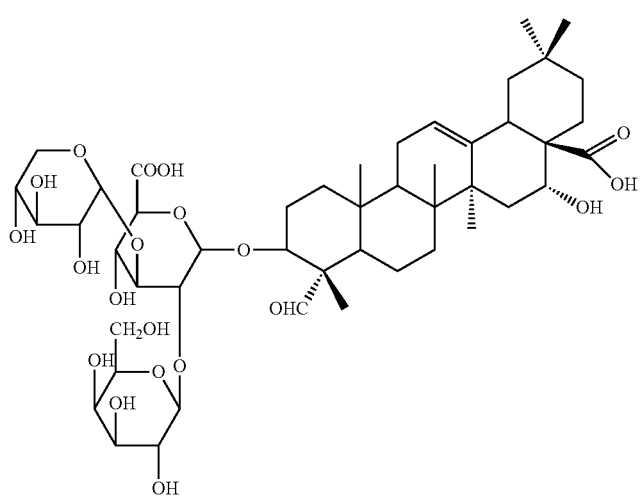 |

In some embodiments, the saponin extract comprises one or more of QS7, QS17, QS18, QS21, DS-1, DS-2, QHA, QHC, and QH-957. In some embodiments, the saponin extract comprises one or more of QS7, QS17, QS18 and QS21. In some embodiments, the saponin extract comprises at least 50% QS7, QS17, QS18 and QS21, at least 60% QS7, QS17, QS18 and QS21, at least 70% QS7, QS17, QS18 and QS21, at least 80% QS7, QS17, QS18 and QS21, at least 90% QS7, QS17, QS18 and QS21, at least 95% QS7, QS17, QS18 and QS21, at least 98% QS7, QS17, QS18 and QS21, or at least 99% QS7, QS17, QS18 and QS21.

In some embodiments, the saponin extract is at least about 5% QS7, at least about 10% QS7, at least about 15% QS7, at least about 20% QS7, at least about 25% QS7, at least about 30% QS7, at least about 35% QS7, at least about 40% QS7, at least about 45% QS7, at least about 50% QS7, at least about 55% QS7, at least about 60% QS7, at least about 65% QS7, at least about 70% QS7, at least about 75% QS7, at least about 80% QS7, at least about 85% QS7, at least about 90% QS7, or at least about 95% QS7.

In some embodiments, the saponin extract is at least about 5% QS17, at least about 10% QS17, at least about 15% QS17, at least about 20% QS17, at least about 25% QS17, at least about 30% QS17, at least about 35% QS17, at least about 40% QS17, at least about 45% QS17, at least about 50% QS17, at least about 55% QS17, at least about 60% QS17, at least about 65% QS17, at least about 70% QS17, at least about 75% QS17, at least about 80% QS17, at least about 85% QS17, at least about 90% QS17, or at least about 95% QS17.

In some embodiments, the saponin extract is at least about 5% QS18, at least about 10% QS18, at least about 15% QS18, at least about 20% QS18, at least about 25% QS18, at least about 30% QS18, at least about 35% QS18, at least about 40% QS18, at least about 45% QS18, at least about 50% QS18, at least about 55% QS18, at least about 60% QS18, at least about 65% QS18, at least about 70% QS18, at least about 75% QS18, at least about 80% QS18, at least about 85% QS18, at least about 90% QS18, or at least about 95% QS18.

In some embodiments, the saponin extract is at least about 5% QS21, at least about 10% QS21, at least about 15%

QS21, at least about 20% QS21, at least about 25% QS21, at least about 30% QS21, at least about 35% QS21, at least about 40% QS21, at least about 45% QS21, at least about 50% QS21, at least about 55% QS21, at least about 60% QS21, at least about 65% QS21, at least about 70% QS21, at least about 75% QS21, at least about 80% QS21, at least about 85% QS21, at least about 90% QS21, or at least about 95% QS21.

In some embodiments, the saponin extract contains not more than 30% QS7, not more than 25% QS7, not more than 20% QS7, not more than 15% QS7, not more than 12% QS7, not more than 10% QS7, not more than 9% QS7, not more than 8% QS7, not more than 7% QS7, not more than 6% QS7, not more than 5% QS7, not more than 4% QS7, not more than 3% QS7, not more than 2.5% QS7, not more than 2% QS7, not more than 1.5% QS7, not more than 1% QS7, not more than 0.5% QS7, not more than 0.1% QS7, or no detectable levels of QS7.

In some embodiments, the saponin extract contains not more than 30% QS17, not more than 25% QS17, not more than 20% QS17, not more than 15% QS17, not more than 12% QS17, not more than 10% QS17, not more than 9% QS17, not more than 8% QS17, not more than 7% QS17, not more than 6% QS17, not more than 5% QS17, not more than 4% QS17, not more than 3% QS17, not more than 2.5% QS17, not more than 2% QS17, not more than 1.5% QS17, not more than 1% QS17, not more than 0.5% QS17, not more than 0.1% QS17, or no detectable levels of QS17.

In some embodiments, the saponin extract contains not more than 30% QS18, not more than 25% QS18, not more than 20% QS18, not more than 15% QS18, not more than 12% QS18, not more than 10% QS18, not more than 9% QS18, not more than 8% QS18, not more than 7% QS18, not more than 6% QS18, not more than 5% QS18, not more than 4% QS18, not more than 3% QS18, not more than 2.5% QS18, not more than 2% QS18, not more than 1.5% QS18, not more than 1% QS18, not more than 0.5% QS18, not more than 0.1% QS18, or no detectable levels of QS18.

In some embodiments, the saponin extract contains not more than 30% QS21, not more than 25% QS21, not more than 20% QS21, not more than 15% QS21, not more than 12% QS21, not more than 10% QS21, not more than 9% QS21, not more than 8% QS21, not more than 7% QS21, not more than 6% QS21, not more than 5% QS21, not more than 4% QS21, not more than 3% QS21, not more than 2.5% QS21, not more than 2% QS21, not more than 1.5% QS21, not more than 1% QS21, not more than 0.5% QS21, not more than 0.1% QS21, or no detectable levels of QS21.

In some embodiments, the saponin extract contains not more than 30% free polysaccharides, not more than 25% free polysaccharides, not more than 20% free polysaccharides, not more than 15% free polysaccharides, not more than 12% free polysaccharides, not more than 10% free polysaccharides, not more than 9% free polysaccharides, not more than 8% free polysaccharides, not more than 7% free polysaccharides, not more than 6% free polysaccharides, not more than 5% free polysaccharides, not more than 4% free polysaccharides, not more than 3% free polysaccharides, not more than 2.5% free polysaccharides, not more than 2% free polysaccharides, not more than 1.5% free polysaccharides, not more than 1% free polysaccharides, not more than 0.5% free polysaccharides, not more than 0.1% free polysaccharides, or no detectable levels of free polysaccharides.

In some embodiments, the saponin extract contains not more than 30% free phenolic compounds, not more than 25% free phenolic compounds, not more than 20% free phenolic compounds, not more than 15% free phenolic compounds, not more than 12% free phenolic compounds, not more than 10% free phenolic compounds, not more than 9% free phenolic compounds, not more than 8% free phenolic compounds, not more than 7% free phenolic compounds, not more than 6% free phenolic compounds, not more than 5% free phenolic compounds, not more than 4% free phenolic compounds, not more than 3% free phenolic compounds, not more than 2.5% free phenolic compounds, not more than 2% free phenolic compounds, not more than 1.5% free phenolic compounds, not more than 1% free phenolic compounds, not more than 0.5% free phenolic compounds, not more than 0.1% free phenolic compounds, or no detectable levels of free phenolic compounds.

In some embodiments, the saponin extract is substantially free of proteins. In some embodiments, the saponin extract is substantially free of polysaccharides. In some embodiments, the saponin extract is substantially free of phenolic compounds.

Optionally, the extraction process is monitored at one or more steps using analytical methods such as HPLC, MS, LC/MS, GC/MS, UPLC, UV/Vis spectrometry, NMR, and/or TLC.

In some embodiments, the extraction procedure is performed at standard pressure. In some embodiments, one or more steps of the procedure are performed at about 0.1 atm; at about 0.5 atm; at about 1 atm; at about 5 atm; at about 10 atm; at about 25 atm; at about 50 atm; at about 100 atm; at about 200 atm; at about 300 atm; at about 400 atm; or at about 500 atm.

In some embodiments, one or more steps are performed at a temperature of at least about 5° C.; at least about 10° C.; at least about 15° C.; at least about 20° C.; at least about 25° C.; at least about 30° C.; at least about 35° C.; at least about 40° C.; at least about 45° C.; at least about 50° C.; at least about 55° C.; at least about 60° C.; at least about 65° C.; at least about 70° C.; at least about 75° C.; at least about 80° C.; at least about 85° C.; at least about 90° C.; at least about 95° C.; at least about 100° C.; at least about 105° C.; or at least about 110° C.

In some embodiments, the extraction procedure is completed in about 2 hours, in about 4 hours, in about 8 hours, in about 16 hours, in about 24 hours, in about 48 hours, in about 96 hours, in about 5 days, in about 1 week, in about 2 weeks, in about 3 weeks, in about 4 weeks, in about 5 weeks, or in about 6 weeks.

EXAMPLES

Example 1

Obtaining Saponins from *Quillaja saponaria* Bark

In FIG. 1, a schematic representation is shown of a preferred embodiment of the complete process to obtain saponins from *Quillaja saponaria* Molina biomass 1 to the liquid product of purified saponins 30 and powder product of purified saponins 32.

For the generation of a plant extract 2, 210 Kg of *Quillaja saponaria* Molina bark 1 previously dried and ground were used, with 1.000 L of soft water 3, which were loaded into different tanks as follows:

a) 70 Kg of bark 1 were added in each of the extraction tanks 4, 5, 6, then 250 L of soft water 3 were added in the tank 4, the content of the tank 4 was heated to 60 degrees Celsius for 3 hours, and an extract was obtained, which was pumped into the tank 5, through the transfer line 7.

b) 250 L of soft water 3 were added again in the tank 4, then the content of the tanks 4 and 5 was heated to 60 degrees Celsius for 3 hours, and an extract from each of these tanks was obtained. The extract from tank 5 was pumped into the tank 6 through the transfer line 8, and the extract from tank 4 was pumped into tank 5, through the transfer line 7.

c) 250 L of soft water 3 were added again in the tank 4, then the content of tanks 4, 5, 6 was heated to 60 degrees Celsius for 3 hours, and an extract of each of these tanks was obtained. The extract from tank 6 was pumped through the transfer line 9 towards the end tank 10, the extract of tank 5 was pumped into the tank 6 through the transfer line 8, and the extract from tank 4 was pumped into the tank 5, through the transfer line 7.

d) 250 L of soft water 3 were added again in the tank 4, then the content of tanks 4, 5, 6 was heated to 60 degrees Celsius for 3 hours, and an extract from each of these tanks was obtained. The extract from tank 6 was pumped into the tank 10 through the transfer line 9, the extract from tank 5 was pumped into the tank 6 through the transfer line 8, and the extract from tank 4 was pumped into the tank 5, through the transfer line 7.

e) Then, the content of tanks 5 and 6 was heated at 60 degrees Celsius for 3 hours, and an extract from each of these tanks was obtained. The extract from tank 6 was pumped into tank 10, through the transfer line 9, and the extract from tank 5 was pumped into the tank 6 through the transfer line 8.

f) Finally, the content of the tank 6 was heated to 60 degrees Celsius for 3 hours, and an extract was obtained, which was pumped into the tank 10 through transfer line 9.

The plant extract 2 that was obtained in the tank 10 was transferred through transfer line 11 into a stirring tank 12. The extract 2 was cooled to 15 degrees Celsius and 2.8 Kg of $CaCl_2$ 13 and 0.46 Kg of $Ca(OH)_2$ 14 were added to neutralize the pH, and stirred for 30 minutes. A volume of 60 L of a solution containing 3.2 Kg of $Na_2HPO_4$ 15 and 0.5 Kg of NaOH 16 were added to the obtained mixture and then stirred for 30 minutes. The obtained mixture was heated at 80 degrees Celsius for 1.5 hours to ensure the precipitation of calcium-polysaccharides complexes, and to eliminate them the mixture was filtered through diatomaceous earth 17. The solution obtained 18 was transferred to a stirring tank 19. The solution 18 was cooled to 15 degrees Celsius and HCl 20 was added to adjust pH in a range between 4.3 and 4.5. An amount 20 Kg of PVPP 21 and 53 L of an aqueous suspension of bentonite 22 (75 g/L) were added and stirred. The resulting mixture was filtered through diatomaceous earth 23 and a clarified extract 24 or extract of purified saponins was obtained, containing 35 to 65 g of extracted solutes per liter.

Water was eliminated from the clarified extract 24 through nanofiltration 25 to produce a concentrated extract containing between 85-100 g of extracted solutes per liter. Then, water and low molecular weight impurities were further removed from the concentrated extract by ultrafiltration 26 (10,000-75,000 Da membrane). When the concentration of solutes in the concentrated extract reached 200-250 g of extracted solutes per liter, it was changed to diafiltration mode 27 to produce a liquid precursor 28 containing 130-150 g of extracted solutes per liter. The purity of saponins from the liquid precursor 28 was in the range of 83-91% w/w on dry solids. The liquid precursor 28 was pasteurized by heating to 86 degrees Celsius for 30 to 120 minutes in a heating tank 29, and a liquid product of purified saponins 30 was obtained. Optionally, the product 30 was subjected to a process of spray drying in an equipment having two nozzles 31 (air inlet temperature, 200 degrees Celsius; air outlet temperature, 105-110 degrees Celsius) and 8-10 Kg of purified saponins were produced as a powder product 32, with a purity in a range between 83-91% w/w on dry solids.

Figure 2:
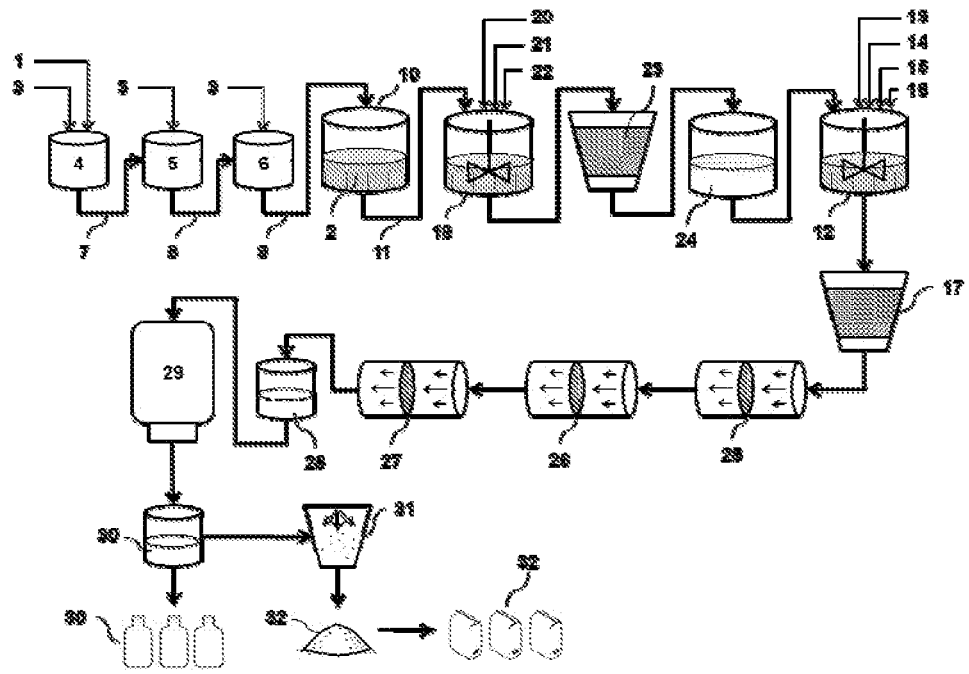
FIG. 2 is a schematic representation of the purification process of saponins from the biomass of *Quillaja saponaria* Molina.

FIG. 2, is a schematic representation of another preferred embodiment of the purification process of saponins from biomass of *Quillaja saponaria* Molina 1, in which, the process of clarification of the plant extract 2 was performed prior to the addition of calcium salts. That is, the plant extract 2 that was obtained in the tank 10, was transferred into a stirring tank 19. The extract 2 was cooled to 15 degrees Celsius and HCl 20 was added to adjust pH to a range between 4.3 and 4.5. PVPP 21 and an aqueous suspension of bentonite 22 (75 g/L) were added and then stirred. The resulting mixture was filtered through diatomaceous earth 23 and a clarified extract 24 was obtained. The clarified extract 24 was cooled to 15 degrees Celsius and $CaCl_2$ 13 and $Ca(OH)_2$ 14 were added to neutralize pH, and then it was stirred for 30 minutes. To the obtained mixture, a solution of $Na_2HPO_4$ 15 and NaOH 16 was added and stirred for 30 more minutes. The mixture obtained was heated to 80 degrees Celsius to ensure precipitation of the calcium-polysaccharides complexes, and to eliminate them the mixture was filtered through diatomaceous earth 17. Reversing these stages did not affect the final result, since it was obtained an extract of saponins with a purity in the range between 83-91% w/w on dry solids, similar to the product obtained by following the steps outlined in FIG. 1.

Example 2

Obtaining Saponins from *Quillaja saponaria* Biomass

In this example, whole-plant biomass from *Quillaja saponaria* Molina 1 was used in contrast to the previous example where only the bark of the plant was used.

For the generation of a plant extract 2, 3,500 Kg of complete *Quillaja saponaria* Molina 1 biomass previously dried and ground was used, with 6,300 L of soft water 3, which were loaded into different tanks following the process described above.

Table 2 shows volume, pH and composition of the plant extract 2 obtained from *Quillaja saponaria* Molina biomass.

TABLE 2

| Characterization of the plant extract 2. | |
|---|---|
| Extract volume | 5,350 L |
| pH | 4.9 |
| Total soluble solids (TSS) concentration | 33 g/Kg |
| Mass fraction of saponins based on dry solids | 26.9% w/w |
| Mass fraction of polysaccharides based on dry solids | 20.0% w/w |
| Mass fraction of polyphenols based on dry solids | 13.1% w/w |

The plant extract 2 obtained in tank 10 was transferred into a stirring tank 12 through transfer line 11. The extract 2 was cooled to 15 degrees Celsius and 7.4 Kg of $CaCl_2$ 13 were added. After the complete dissolution of the calcium salt, 1.8 Kg of $Ca(OH)_2$ powder 14 were added to increase the pH to 7.0. After homogenization of this mixture, 154 L of solution containing 8.2 Kg of $Na_2HPO_4$ 15 and 1.3 Kg of NaOH 16 were added and stirred for 30 minutes. This mixture was heated to 80 degrees Celsius for 1.5 hours and then filtered through diatomaceous earth 17 to produce a solution 18, which is transferred to a stirring tank 19. The solution 18 was cooled to 15 degrees Celsius and HCl 20 was added to adjust the pH in a range between 4.3 and 4.5. An amount of 45 Kg of PVPP 21 and 120 L of an aqueous suspension of bentonite 22 (75 g/L) were added and stirred. The resulting mixture was filtered through diatomaceous earth 23 and a clarified extract 24 or extract of purified saponins was obtained, containing between 25 to 35 g of extracted solutes per liter.

Water was eliminated from the clarified extract 24 through nanofiltration 25 to produce a concentrated extract containing between 85-100 g of extracted solutes per liter. Then, water and low molecular weight impurities were further removed from the concentrated extract by ultrafiltration 26 (10,000-75,000 Da membrane). When the concentration of solutes in the concentrated extract reached 200-250 g of extracted solutes per liter, it was changed to diafiltration mode 27 to produce a liquid precursor 28 containing 130-150 g of extracted solutes per liter. The purity of saponins from the liquid precursor 28 was in the range of 83-91% w/w on dry solids. The liquid precursor 28 was pasteurized by heating to 86 degrees Celsius for 30 to 120 minutes in a heating tank 29, and a liquid product of purified saponins 30 was obtained. Optionally, the product 30 was subjected to a process of spray drying in an equipment having two nozzles 31 (air inlet temperature, 200 degrees Celsius; air outlet temperature, 105-110 degrees Celsius) and 33-38 Kg of purified saponins were produced as a powder product 32, with a purity in a range between 86-94% w/w on dry solids. Table 3 shows a detail of characteristics of the obtained product.

TABLE 3

Characterization of the powder product 32 from Example 2.

| | |
|---|---|
| Mass of powder product | 33-38 Kg |
| Mass fraction of saponins based on dry solids | 86-94% w/w |
| Mass fraction of polysaccharides based on dry solids | <3.5% w/w |
| Mass fraction of polyphenols based on dry solids | <1.3% w/w |

Example 3

Obtaining Saponins from a Powder Product Derived from *Quillaja saponaria*

Figure 3:
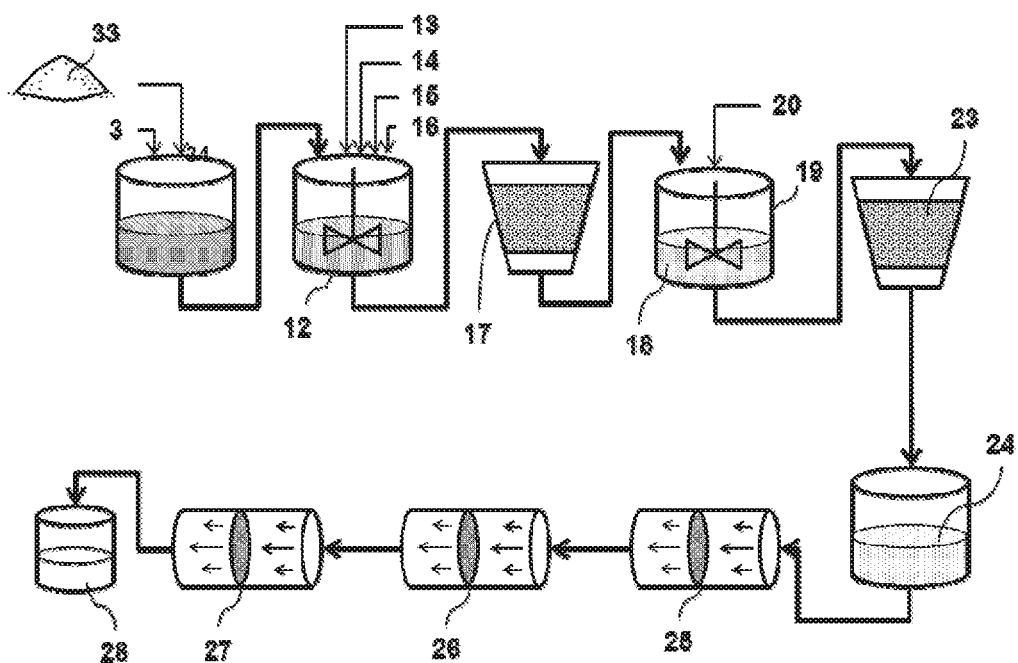
FIG. 3 is a schematic representation of the purification process of saponins from a product containing saponins, which is obtained by the conventional process.

In this example an amount of 60 Kg of powder product 33 of *Quillaja saponaria* Molina saponins was used, which were extracted and purified using a standard conventional method; the product was dissolved in soft water 3 to produce a solution of a conventional product 34. The conventional product 34 is characterized in Table 4, and a scheme of this embodiment of the application is shown in FIG. 3.

The solution of conventional product 34 was cooled to 15 degrees Celsius in a stirring tank 12 and 2.5 Kg of CaCl$_2$ 13 were added. After complete dissolution of this calcium salt, an amount of 0.5-1.5 Kg of Ca(OH)$_2$ powder 14 was added to neutralize the pH. After homogenization of this mixture, 60 L of solution containing 3.0 Kg of Na$_2$HPO$_4$ 15 and 0.5 Kg of NaOH 16 were added and stirred for 30 minutes. This mixture was heated to 80 degrees Celsius and filtered through diatomaceous earth 17 to produce a solution 18. This solution 18 was cooled to 15 degrees Celsius in a stirring tank 19 and 25 Kg of PVPP 21 were added and stirred. The resulting mixture was filtered through diatomaceous earth 23 and a clarified extract 24 or extract of purified saponins was obtained. This extract 24 was subjected to nanofiltration 25, ultrafiltration 26 and diafiltration 27 processes to produce a liquid precursor 28, characterized in Table 4.

TABLE 4

Characterization of the solution of conventional product 34 and the liquid precursor 28.

| | Solution of conventional product 34 | Liquid precursor 28 |
|---|---|---|
| Concentration of solids | 230 g/Kg | 145.5 g/Kg |
| Mass fraction of saponins based on dry solids | 43.5% w/w | 55.5% w/w |
| Mass fraction of polysaccharides based on dry solids | 12.0% w/w | 1.8% w/w |
| Mass fraction of polyphenols based on dry solids | 7.4% w/w | 1.2% w/w |

Example 4

Obtaining Saponins from Biomass

Figure 4:
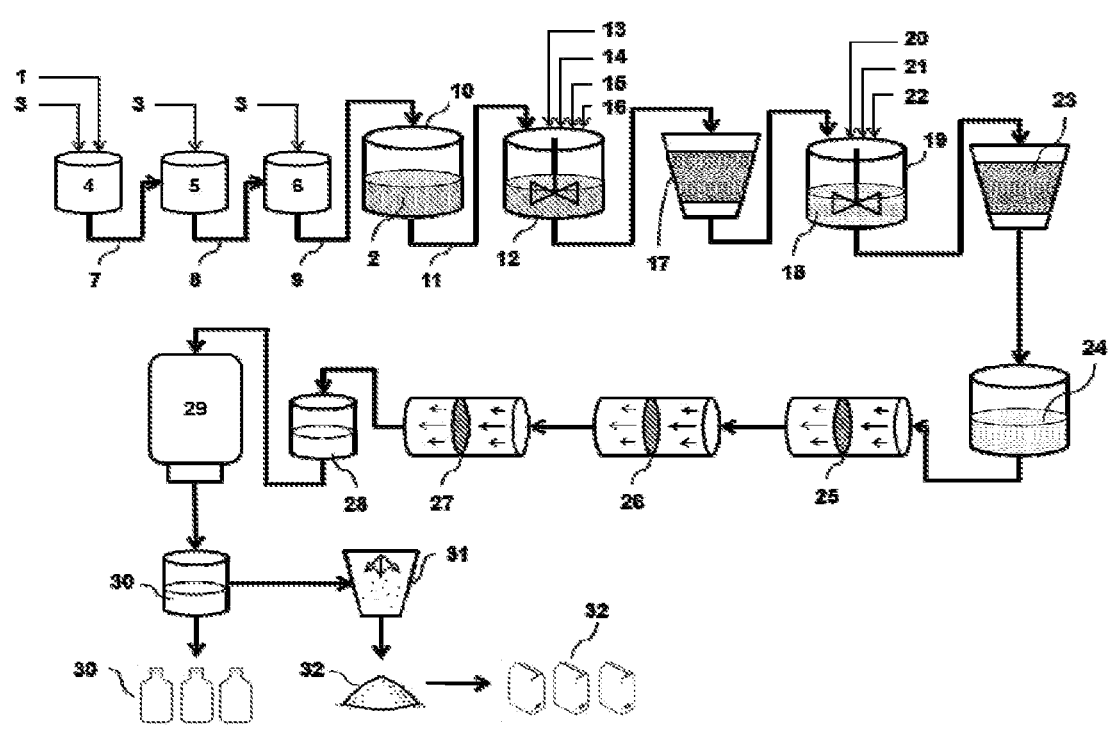
FIG. 4 is a generic schematic representation is shown of the complete process to obtain saponins from whole-plant biomass to the liquid and powdered purified saponin products.

In FIG. 4, a generic schematic representation is shown of the complete process to obtain saponins from whole-plant biomass 1 to the liquid product of purified saponins 30 and powder product of purified saponins 32.

For the generation of a plant extract 2, biomass 1 previously dried and ground is used, with solvent 3, which is loaded into different tanks as follows:

a) biomass 1 is added in each of the extraction tanks 4, 5, 6, then solvent 3 is added in the tank 4, the content of the tank 4 is heated to between 30-100° C. for 1-10 hours, and an extract is obtained, which is pumped into the tank 5, through the transfer line 7.

b) solvent 3 is added again in the tank 4, then the content of the tanks 4 and 5 is heated to between 30-100° C. for 1-10 hours, and an extract from each of these tanks is obtained. The extract from tank 5 is pumped into the tank 6 through the transfer line 8, and the extract from tank 4 is pumped into tank 5, through the transfer line 7.

c) solvent 3 is added again in the tank 4, then the content of tanks 4, 5, 6 is heated to between 30-100° C. for 1-10 hours, and an extract of each of these tanks is obtained. The extract from tank 6 is pumped through the transfer line 9 towards the end tank 10, the extract of tank 5 is pumped into the tank 6 through the transfer line 8, and the extract from tank 4 is pumped into the tank 5, through the transfer line 7.

d) solvent 3 is added again in the tank 4, then the content of tanks 4, 5, 6 is heated to between 30-100° C. for 1-10 hours, and an extract from each of these tanks is obtained. The extract from tank 6 is pumped into the tank 10 through the transfer line 9, the extract from tank 5 is pumped into the tank 6 through the transfer line 8, and the extract from tank 4 is pumped into the tank 5, through the transfer line 7.

e) Then, the content of tanks 5 and 6 is heated at between 30-100° C. for 1-10 hours, and an extract from each of these tanks is obtained. The extract from tank 6 is pumped into tank 10, through the transfer line 9, and the extract from tank 5 is pumped into the tank 6 through the transfer line 8. Any of tanks 4, 5, and/or 6 may be pressurized from 0.1 atm up to 100 atm.

f) Finally, the content of the tank 6 is heated to between 30-100° C. for 1-10 hours, and an extract is obtained, which is pumped into the tank 10 through transfer line 9.

The plant extract 2 in tank 10 is transferred through transfer line 11 into a stirring tank 12. The extract 2 is cooled to 5-15° C. and a salt 13 and base 14 are added to adjust the pH, and stirred for 30 minutes. A solution containing a salt 15 and another base 16 is added to the mixture and stirred for 30 minutes. The mixture is heated at 60-100° C. for 0.5-3 hours and the mixture is filtered through diatomaceous earth 17. The solution 18 is transferred to a stirring tank 19. The solution 18 is cooled to 5-15° C. and an acid 20 is added to adjust pH. A first polymeric adsorbent 21 and an aqueous suspension of a clay adsorbent 22 is added with stirring. The resulting mixture is filtered through diatomaceous earth 23 and a clarified extract 24 or extract of purified saponins is obtained.

Solvent is eliminated from the clarified extract 24 through nanofiltration 25 to produce a concentrated extract containing between 85-100 g of extracted solutes per liter. Then, solvent and low molecular weight impurities is further removed from the concentrated extract by ultrafiltration 26 (10,000-75,000 Da membrane). When the concentration of solutes in the concentrated extract reached 200-250 g of extracted solutes per liter, it is changed to diafiltration mode 27 to produce a liquid precursor 28 containing 130-150 g of extracted solutes per liter. The purity of saponins from the liquid precursor 28 is in the range of 60-99.9% w/w on dry solids. The liquid precursor 28 is pasteurized by heating to 86° C. for 30 to 120 minutes in a heating tank 29, and a liquid product of purified saponins 30 is obtained. A portion of the product 30 is subjected to a process of spray drying in a drying equipment to obtain a powder product 32, with a purity in a range between 80-99.9% w/w on dry solids. Any of tanks 4, 5, 6, 12, 19, and/or 29 may be pressurized from 0.1 atm up to 100 atm.

One or more of the individually-identified steps are contemplated as processes within the scope of this disclosure.

What is claimed is:

1. A plant extract mixture comprising:
   a) saponins,
   b) a salt,
   c) a solvent,
   d) a phosphate, and
   e) precipitated polysaccharides, wherein the mixture has a pH between 4 and 7, and, wherein the salt of b) is a lithium salt, a strontium salt, a barium salt, a chromium salt, a manganese salt, an iron salt, a cobalt salt, a nickel salt, a copper salt, a zinc salt, an aluminum salt, a silver salt, or a combination of the foregoing.

2. The mixture of claim 1, wherein the salt is selected from $SrCl_2$, $BaCl_2$, SrBr2, BaBr2 or a combination thereof.

3. The mixture of claim 1, wherein the solvent is a polar protic solvent.

4. The mixture of claim 1, wherein the solvent is selected from acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme, 1,2-dimethoxyethane, dimethylformamide, dimethylsulfoxide, 1,4-dioxane, ethanol, ethyl acetate, ethylene glycol, glycerin, heptane, hexamethylphosphoramide, hexamethylphosphorous triamde, hexane, methanol, methyl-t-butyl ether, methylene chloride, N-methyl-2-pyrrolidinone, pentane, perchloroethylene, petroleum ether, 1-propanol, 2-propanol, pyridine, tetrahydrofuran, toluene, triethylamine, trifluorotoluene, water, xylene, or any combination of the forgoing.

5. The mixture of claim 4, wherein the solvent is water.

6. The mixture of claim 1, wherein the phosphate is an alkali metal phosphate or an alkaline earth phosphate.

7. The mixture of claim 1, wherein the phosphate is a lithium phosphate, sodium phosphate, potassium phosphate, barium phosphate, magnesium phosphate, calcium phosphate, cesium phosphate, lithium hydrogen phosphate, sodium hydrogen phosphate, potassium hydrogen phosphate, barium hydrogen phosphate, magnesium hydrogen phosphate, calcium hydrogen phosphate, cesium hydrogen phosphate, lithium dihydrogen phosphate, sodium dihydrogen phosphate, or potassium dihydrogen phosphate.

8. The mixture of claim 1, wherein said mixture comprises not more than 30% dissolved polysaccharides.

9. The mixture of claim 1, further comprising a sodium salt, a potassium salt, a magnesium salt, a calcium salt, or a combination thereof.

10. The mixture of claim 9, wherein the salt is selected from NaCl, KCl, $MgCl_2$, $CaCl_2$, $MgBr_2$, $CaBr_2$, or a combination thereof.

* * * * *